(12) United States Patent
Arramon

(10) Patent No.: US 10,441,431 B2
(45) Date of Patent: Oct. 15, 2019

(54) ANATOMY ACCOMODATING PROSTHETIC INTERVERTEBRAL DISC WITH LOWER HEIGHT

(71) Applicant: Simplify Medical Pty Limited, Mountain View, CA (US)

(72) Inventor: Yves Arramon, Sunnyvale, CA (US)

(73) Assignee: Simplify Medical Pty Ltd (AU)

( * ) Notice: Subject to any disclaimer, the term of this patent is extended or adjusted under 35 U.S.C. 154(b) by 22 days.

(21) Appl. No.: 15/230,116

(22) Filed: Aug. 5, 2016

(65) Prior Publication Data

US 2016/0338848 A1 Nov. 24, 2016

Related U.S. Application Data

(63) Continuation of application No. 14/339,280, filed on Jul. 23, 2014, now Pat. No. 9,421,107, which is a (Continued)

(51) Int. Cl.
*A61F 2/44* (2006.01)
*A61F 2/30* (2006.01)

(52) U.S. Cl.
CPC ........ *A61F 2/4425* (2013.01); *A61F 2/30965* (2013.01); *A61F 2002/305* (2013.01); (Continued)

(58) Field of Classification Search
CPC .............. A61F 2/4425; A61F 2002/443; A61F 2220/0025; A61F 2/44; A61F 2/442
(Continued)

(56) References Cited

U.S. PATENT DOCUMENTS 7,442,211 B2 10/2008 De Villiers et al.
7,531,001 B2 5/2009 De Villiers et al.
(Continued)

OTHER PUBLICATIONS

European search report and opinion dated Mar. 30, 2015 for EP Application No. 12839988.8.
(Continued)

*Primary Examiner* — Eduardo C Robert
*Assistant Examiner* — Christina Negrellirodriguez
(74) *Attorney, Agent, or Firm* — Wilson Sonsini Goodrich & Rosati

(57) ABSTRACT

An intervertebral disc includes a superior endplate having an upper vertebral contacting surface and a lower bearing surface, wherein the upper vertebral contacting surface of the superior endplate has a central portion that is raised relative to a peripheral portion of the superior endplate, and wherein the lower bearing surface has a concavity disposed opposite the raised central portion. The disc includes an inferior endplate having a lower vertebral contacting surface and an upper surface, wherein the lower vertebral contacting surface of the inferior endplate has a central portion and wherein the upper bearing surface has a concavity disposed opposite the central portion. A core is positioned between the superior and inferior endplates, the core having upper and lower core bearing surfaces configured to mate with the bearing surfaces of the superior and inferior endplates. The upper vertebral contacting surface of the superior endplate has a different shape than the lower vertebral contacting surface of the inferior endplate.

18 Claims, 6 Drawing Sheets

Related U.S. Application Data continuation of application No. 13/647,933, filed on Oct. 9, 2012, now Pat. No. 8,808,384.

(60) Provisional application No. 61/546,848, filed on Oct. 13, 2011.

(52) U.S. Cl.
CPC ............ *A61F 2002/30024* (2013.01); *A61F 2002/3065* (2013.01); *A61F 2002/30153* (2013.01); *A61F 2002/30448* (2013.01); *A61F 2002/30451* (2013.01); *A61F 2002/30563* (2013.01); *A61F 2002/30607* (2013.01); *A61F 2002/30616* (2013.01); *A61F 2002/30649* (2013.01); *A61F 2002/30654* (2013.01); *A61F 2002/30662* (2013.01); *A61F 2002/30843* (2013.01); *A61F 2002/30884* (2013.01); *A61F 2002/30904* (2013.01); *A61F 2002/443* (2013.01); *A61F 2220/0016* (2013.01); *A61F 2310/00011* (2013.01); *A61F 2310/00017* (2013.01); *A61F 2310/00023* (2013.01); *A61F 2310/00029* (2013.01); *A61F 2310/0088* (2013.01); *A61F 2310/00131* (2013.01); *A61F 2310/00179* (2013.01); *A61F 2310/00323* (2013.01); *A61F 2310/00407* (2013.01); *A61F 2310/00604* (2013.01); *A61F 2310/00796* (2013.01)

(58) Field of Classification Search
USPC ............ 606/246–249; 623/17.11–17.16
See application file for complete search history.

(56) References Cited

U.S. PATENT DOCUMENTS

| | | | |
|---|---|---|---|
| 7,695,517 B2* | 4/2010 | Benzel | A61F 2/4611 623/17.11 |
| 7,753,956 B2 | 7/2010 | De Villiers et al. | |
| 7,875,080 B2* | 1/2011 | Puno | A61F 2/30771 623/17.16 |
| 7,959,678 B2 | 6/2011 | Filippi et al. | |
| 8,808,384 B2 | 8/2014 | Arramon | |
| 9,421,107 B2 | 8/2016 | Arramon et al. | |
| 2003/0135277 A1 | 7/2003 | Bryan et al. | |
| 2004/0111155 A1 | 6/2004 | Ferree | |
| 2005/0149189 A1 | 7/2005 | Mokhtar et al. | |
| 2005/0261772 A1 | 11/2005 | Filippi et al. | |
| 2006/0069437 A1 | 3/2006 | Weber | |
| 2006/0142862 A1 | 6/2006 | Diaz et al. | |
| 2006/0287728 A1 | 12/2006 | Mokhtar et al. | |
| 2007/0073403 A1 | 3/2007 | Lombardo et al. | |
| 2007/0162130 A1 | 7/2007 | Rashbaum et al. | |
| 2007/0282449 A1 | 12/2007 | De Villiers et al. | |
| 2008/0033554 A1 | 2/2008 | Lechmann et al. | |
| 2008/0051901 A1 | 2/2008 | De Villiers et al. | |
| 2008/0114453 A1 | 5/2008 | Francis | |
| 2009/0234458 A1* | 9/2009 | de Villiers | A61F 2/30771 623/17.16 |
| 2009/0276051 A1 | 11/2009 | Arramon et al. | |
| 2010/0016972 A1 | 1/2010 | Jansen et al. | |
| 2010/0016973 A1 | 1/2010 | De Villiers et al. | |
| 2013/0274880 A1 | 10/2013 | Arramon | |

OTHER PUBLICATIONS

International search report and written opinion dated Mar. 25, 2013 for PCT/US2012/059401.
Notice of allowance dated Jun. 23, 2014 for U.S. Appl. No. 13/647,933.
Office action dated May 8, 2014 for U.S. Appl. No. 13/647,933.
Office action dated Aug. 15, 2014 for U.S. Appl. No. 14/339,280.
Office action dated Oct. 15, 2015 for U.S. Appl. No. 14/339,280.
Office action dated May 7, 2015 for U.S. Appl. No. 14/339,280.
Notice of allowance dated Jun. 2, 2012 for U.S. Appl. No. 14/339,280.

* cited by examiner

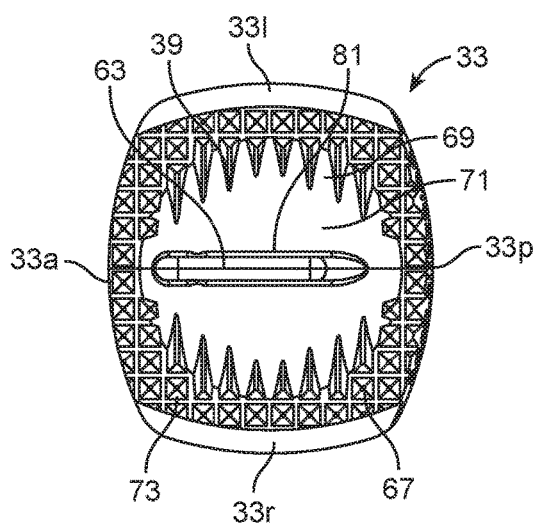
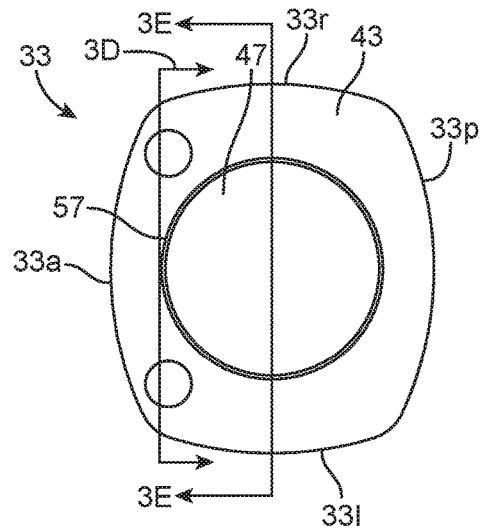
FIG. 3A  FIG. 3B
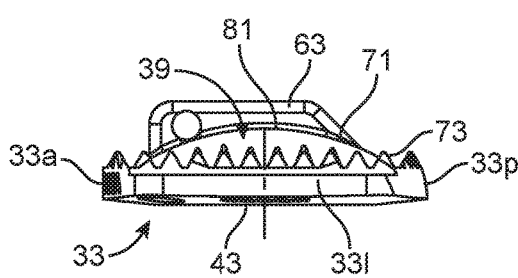
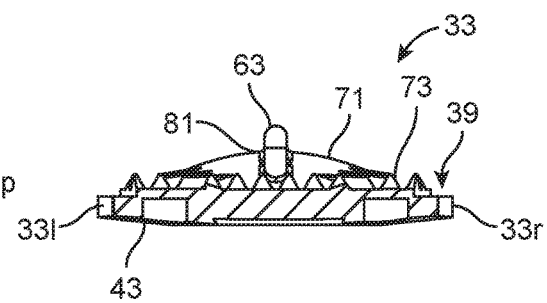
FIG. 3C  FIG. 3D
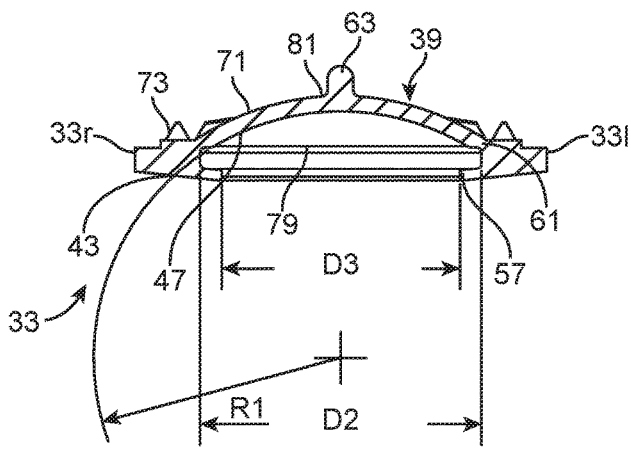
FIG. 3E

ANATOMY ACCOMODATING PROSTHETIC INTERVERTEBRAL DISC WITH LOWER HEIGHT

CROSS-REFERENCE TO RELATED APPLICATIONS

The present application is a continuation of U.S. patent application Ser. No. 14/339,280, filed Jul. 23, 2014, now U.S. Pat. No. 9,421,107, which is a continuation of U.S. patent application Ser. No. 13/647,933, filed Oct. 9, 2012, which claims the benefit of U.S. Provisional Application No. 61/546,848, filed Oct. 13, 2011, the entire contents of which are incorporated herein by reference.

BACKGROUND AND SUMMARY OF THE INVENTION

The present invention relates to medical devices and methods. More specifically, the invention relates to intervertebral prosthetic discs and methods of preserving motion upon removal of an intervertebral disc.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral disc cause a patient pain and discomfort, surgery is often required. Traditionally, surgical procedures for treating intervertebral discs have involved discectomy (partial or total removal of a disc), with or without interbody fusion of the two vertebrae adjacent to the disc. When the disc is partially or completely removed, it is necessary to replace the excised disc material with natural bone or artificial support structures to prevent direct contact between hard bony surfaces of adjacent vertebrae. Oftentimes, pins, rods, screws, cages and/or the like are inserted between the vertebrae to act as support structures to hold the vertebrae and any graft material in place while the bones permanently fuse together.

A more recent alternative to traditional fusion is total disc replacement or TDR. TDR provides the ability to treat disc related pain without fusion provided by bridging bone, by using a movable, implantable, artificial intervertebral disc (or "disc prosthesis") between two vertebrae. A number of different artificial intervertebral discs are currently being developed. For example, U.S. Pat. Nos. 7,442,211; 7,531,001 and 7,753,956 and U.S. Patent Application Publication Nos. 2007/0282449; 2009/0234458; 2009/0276051; 2010/0016972 and 2010/0016973 which are hereby incorporated by reference in their entirety, describe artificial intervertebral discs with mobile bearing designs. Other examples of intervertebral disc prostheses are the Charité® disc (provided by DePuy Spine, Inc.) MOBIDISC® (provided by LDR Medical (www.ldrmedical.fr)), the BRYAN Cervical Disc (provided by Medtronic Sofamor Danek, Inc.), the PRODISC® or PRODISC-C® (from Synthes Stratec, Inc.), the PCM disc (provided by Cervitech, Inc.), and the MAVERICK® disc (provided by Medtronic Sofomor Danek).

These known artificial intervertebral discs generally include superior and inferior endplates which locate against and engage the adjacent vertebral bodies, and a core for providing motion between the plates. The core may be movable or fixed, metallic, ceramic or polymer and generally has at least one convex outer surface which mates with a concave recess on one of the plates in a fixed core device or both of the plates for a movable core device. In order to implant these intervertebral discs, the natural disc is removed and the vertebrae are distracted or forced apart in order to fit the artificial disc in place. Depending on the size of the disc space, many of the known artificial discs have a height which is higher than desired resulting in an unnaturally over distracted condition upon implantation of the disc. For example, a smallest height disc available can be about 10-13 mm for lumbar discs and about 5-6 mm for cervical discs.

Currently available artificial intervertebral discs do not provide a desired low profile for some patients with smaller disc heights. It would be desirable to provide a lower height disc which mimics more closely the natural anatomy for smaller patients.

In addition, the vertebral body contacting surfaces of many of the known artificial discs are flat. The inventor has recognized that this flat configuration does not generally match the surfaces of the vertebral bodies resulting in less than ideal bone to implant contact surfaces. It would be desirable to provide a more anatomically shaped vertebral body contacting surface for an artificial disc.

According to an aspect of the present invention, an intervertebral disc comprises: a superior endplate having an upper vertebra contacting surface and a lower bearing surface, wherein the upper surface of the upper endplate has a domed central portion and wherein the lower bearing surface has a concavity disposed opposite the domed central portion; an inferior endplate having a lower vertebra contacting surface and an upper surface, wherein the lower surface of the lower endplate has a domed central portion and wherein the upper bearing surface has a concavity disposed opposite the domed central portion; a core positioned between the superior and inferior endplates, the core having upper and lower surfaces configured to mate with the bearing surfaces of the superior and inferior endplates; and wherein the domed central portion of the superior endplate has a height greater than a height of the domed central portion of the inferior endplate.

According to another aspect of the present invention, an intervertebral disc comprises: a superior endplate having an upper vertebral contacting surface and a lower bearing surface, wherein the upper vertebral contacting surface of the superior endplate has a central portion that is raised relative to a peripheral portion of the superior endplate, and wherein the lower bearing surface has a concavity disposed opposite the raised central portion; an inferior endplate having a lower vertebral contacting surface and an upper surface, wherein the lower vertebral contacting surface of the inferior endplate has a central portion that is raised relative to a peripheral portion of the inferior endplate and wherein the upper bearing surface has a concavity disposed opposite the central portion; and a core positioned between the upper and inferior endplates, the core having upper and lower core bearing surfaces configured to mate with the bearing surfaces of the upper and inferior endplates; wherein the upper vertebral contacting surface of the superior endplate has a different shape than the lower vertebral contacting surface of the inferior endplate.

BRIEF DESCRIPTION OF THE DRAWINGS

The features and advantages of the present invention are well understood by reading the following detailed description in conjunction with the drawings in which like numerals indicate similar elements and in which:

FIGS. 3A-3E are top, bottom, side, anterior cross-sectional, and side cross-sectional views, respectively, of a superior endplate of an intervertebral disc according to an aspect of the present invention;

DETAILED DESCRIPTION

Figure 1A:
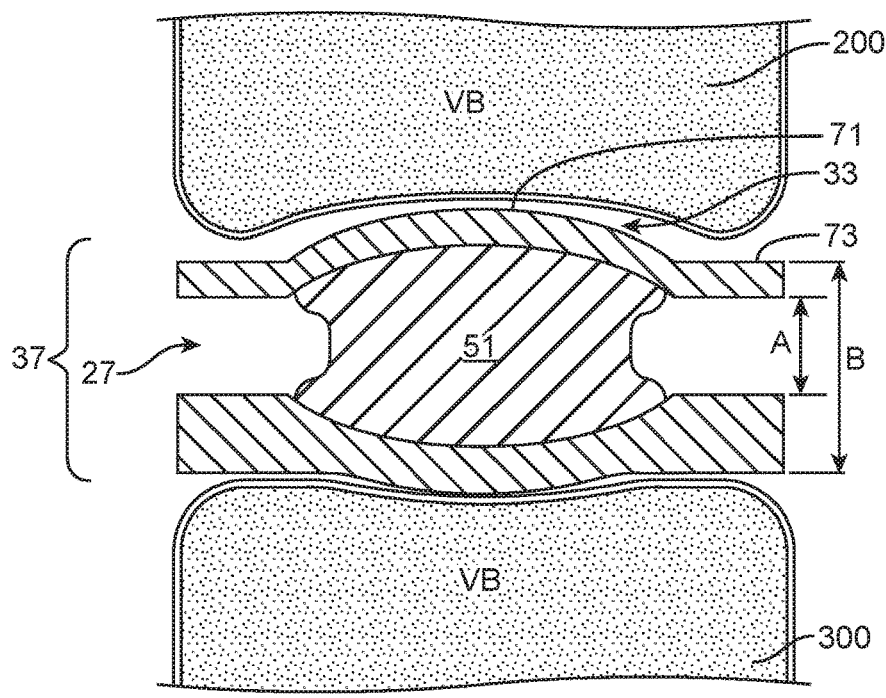
FIG. 1A is a schematic cross-sectional view of a vertebra including an intervertebral disc according to an aspect of the present invention.
Figure 1B:
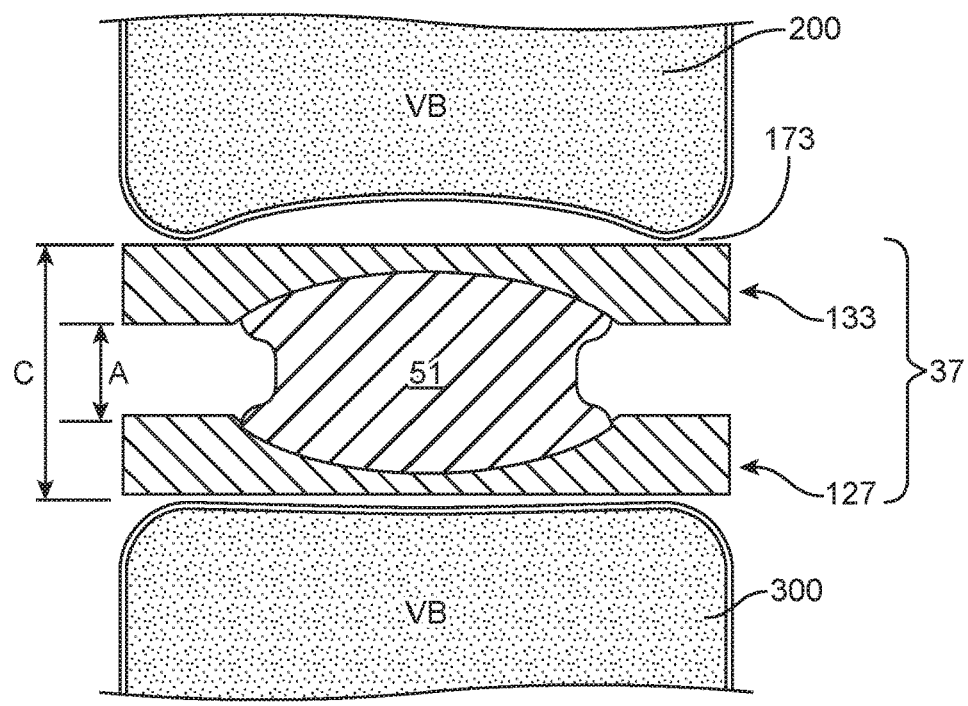
FIG. 1B is a schematic cross-sectional view of a vertebra including an intervertebral disc according to the prior art.
Figure 2A:
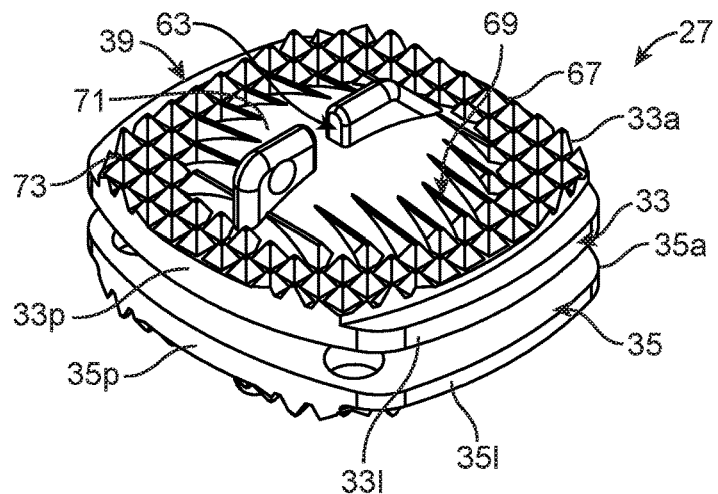
FIGS. 2A-2C are top perspective, side, and side, cross-sectional views, respectively, of an intervertebral disc according to an aspect of the present invention.
Figure 2B:
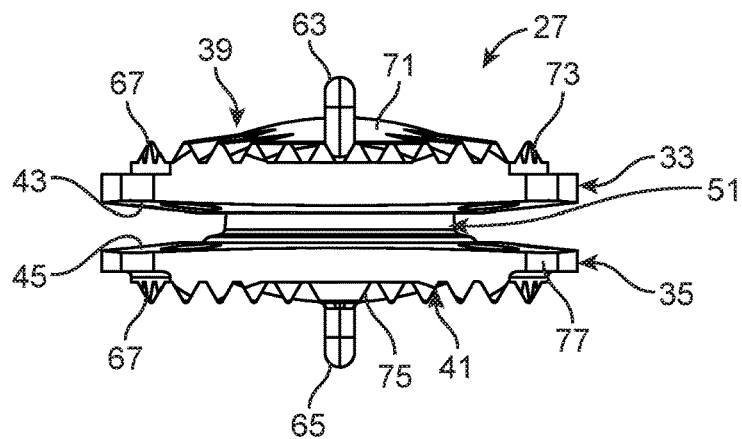
Figure 2C:
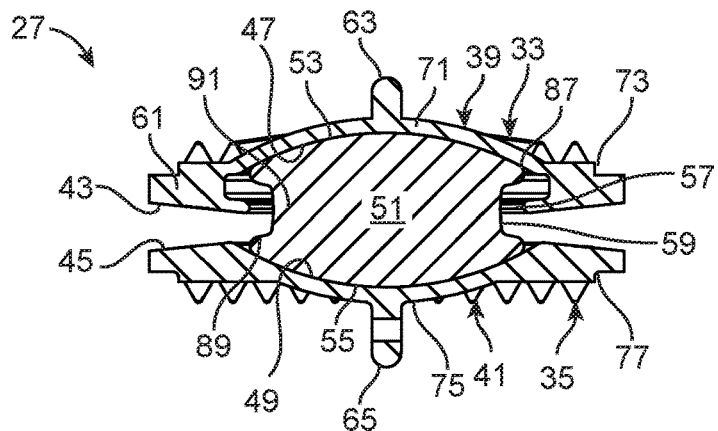

FIGS. 2A-2C show an intervertebral disc 27 that comprises superior and inferior endplates 33 and 35 that, as seen in FIG. 1A, are sized and shaped to fit within an intervertebral space 37. Each endplate 33 and 35 has a vertebral contacting surface 39 and 41, respectively, and an inner surface 43 and 45, respectively. As seen in the cross section of FIG. 2C, the superior endplate 33 has a first or lower bearing surface 47 on the inner or lower surface 43 of the superior endplate, and the inferior endplate 35 has a second or upper bearing surface 49 on the inner or upper surface 45 of the inferior endplate. The bearing surfaces 47 and 49 are spherical in shape, however other known bearing surface shapes may also be used.

A mobile core 51 is configured to be received between the first and second bearing surfaces 47 and 49. The core 51 has at least one, ordinarily two, curved bearing surfaces 53 and 55. The core 51 is ordinarily rigid, i.e., substantially inflexible and incompressible, however, the core may be flexible, compressible, and/or compliant with rigid bearing surfaces. In the embodiment shown in FIG. 2A-2C, the core 51 is rigid and has first and second curved bearing surfaces 53 and 55 for contacting the first and second curved bearing surfaces 47 and 49, respectively, of the superior and inferior endplates. The superior and inferior endplates 33 and 35 are articulable and rotatable relative to each other via sliding motion of at least one of, ordinarily both of, the first and second bearing surfaces 47 and 49 over the core 51.

The inventor has recognized that providing raised or domed central portions of both the upper vertebral contacting surface 39 and the lower vertebral contacting surface 41, the disc can be made smaller and closer in size to the natural disc providing more nearly natural motion. The inventor has also recognized that the raised or domed central portions can be advantageously raised in different amounts, to more accurately match the anatomy of the majority of patients while further reducing the height of the disc. Matching the natural disc height accurately leads to more natural motion while overstuffing a large disc in a small disc space can lead to limited motion.

Discs which are too large for the size of a disc space of a patient are thought to be detrimental to the patient. A connection has been found between fusion (no motion) at a disc level and increased degenerative disc disease at adjacent disc levels. This leads to the conclusion that overly large discs with limited mobility may also result in increases in degenerative disc disease at adjacent levels. Placing a disc which is too large for the disc space can also result in the unwanted result of migration sometimes leading to removal of the disc.

In one embodiment of an intervertebral disc system designed for use in the cervical spine, a core has a diameter of about 8-10 mm, a height of about 4-6 mm, and a spherical radius of curvature of the bearing surfaces of about 10-18 mm. The intervertebral discs 27 and 29 may be provided in different heights to accommodate patient anatomy. For example, discs may be provided in multiple heights, such as of 4, 5, 6 and 7 mm or in other size variations. The discs may also be provided in different sizes. In one example, for example different lengths in the anterior/posterior direction can be used to accommodate different anatomies. Although different width discs can be used, in the preferred embodiment, the width of the discs is approximately the same for the different disc sizes. The same core 51 and bearing surface configuration is preferably use in the discs of multiple sizes In another embodiment of an intervertebral disc system designed for use in the lumbar spine, a core has a diameter of about 10-15 mm, a height of about 5-10 mm, and a spherical radius of curvature of the bearing surfaces of about 10-18 mm.

The superior endplate 33 (shown in FIGS. 3A-3E) and the inferior endplate 35 (shown in FIGS. 4A-4E) each have left and right longitudinal sides 33*l* and 33*r* and 35*l* and 35*r*, when the disc is viewed from the anterior, and anterior and posterior ends 33*a* and 33*p* and 35*a* and 35*p*.

At least the superior endplate 33 includes a projection 57 which engages with a recess 59 of the core 51 to retain the core between the superior and inferior endplates 33 and 35. The projection 57 can be in the form of an annular rim having a diameter D3 (FIG. 3E) and the recess 59 can be in the form of an annular groove, usually having diameter equal to or slightly less than the diameter D3. In the embodiments shown in FIGS. 1-3 and 6, the projection 57 extends 360° around the core 51. The core and the projection are ordinarily shaped so that the part of the core below the recess can be passed through an opening defined by the projection in a direction substantially along an axis of the opening defined by the projection. In the embodiments illustrated, the endplate 33 having the retaining ring or projection 57 has been illustrated as the superior endplate. However, it should be understood that the inferior endplate 35 can be provided with a projection instead of or in addition to having the projection on the superior endplate. Ordinarily, however, each endplate will not have a projection to keep thickness of the disc to a minimum and to increase range of motion of the endplate without a projection relative to the core and the endplates relative to each other.

In addition to permitting sliding motion, the core 51 is movable with respect to both of the superior and inferior endplates 33 and 35. "Movable" is specifically defined for purposes of describing the movability of the core 51 with respect to at least one of the superior and inferior endplates 33 and 35 as meaning that the core is adapted to be displaced in a direction toward or away from at least one of the left and right longitudinal sides 33l and 33r and 35l and 35r and anterior and posterior ends 33a and 33p and 35a and 35p of at least one of superior and inferior endplates. The core 51 is movable with respect to both the superior and inferior endplates when the intervertebral disc system is in use implanted between the vertebrae of a patient. However, the core 51 may have a non-movable position when the disc is being implanted or before completion of a surgical implantation procedure. In a preferred embodiment, the core 51 is movable with respect to both the superior and inferior endplates in both the anterior-posterior direction and the left-right direction Although the radius of curvature of the bearing surfaces of the core and the bearing surfaces of the plates 47 and 49, as shown, are substantially the same (substantially congruent) for purposes of distribution of load and reduced wear, in other embodiments, at least one of the first and second bearing surfaces 47 and 49, or the bearing surfaces of the core can be modified with a groove, channel, depression or flat on a portion of the bearing surface.

Instead of providing two curved bearing surfaces on the core and corresponding curved bearing surfaces on the superior and inferior endplates, one of the bearing surfaces may be another shape, such as substantially flat (not shown). For example, the top bearing surface on the core below the recess can be flat and the lower bearing surface on the superior endplate above the projection can be flat. The first bearing surface on the superior endplate can be larger than the first bearing surface on the core to facilitate limited translational movement of the core relative to the superior endplate. If the second bearing surface on the inferior endplate and the second bearing surface on the core are curved, the superior and inferior endplates will be articulable and rotatable relative to each other via sliding motion. In another example, the first bearing surface 47 on the inner surface 43 of the superior endplate and corresponding bearing surface 53 on the core 51 can be flat while the upper bearing surface 49 on the upper surface 45 of the inferior endplate 35 and the corresponding bearing surface 55 of the core can be cylindrically curved in a direction to allow anterior posterior rotation of the upper endplate. Other bearing surface shapes which can also be used depending on the type of motion of the mobile core desired including trough shaped, kidney bean shaped, elliptical, or oval bearing surfaces.

As seen, for example, in FIGS. 2A, 3A, 3C, the superior and inferior endplates 33 and 35 can each include one or more elongated fins or keels 63 and 65, respectively, on the vertebral contacting surface 39 and 41, respectively, thereof. If a single, central fin is provided, there will be less cutting of bone required during insertion. However, if multiple, usually two, fins, are provided on one or more of the endplates or if a fin has a break 63' between forward and rear components (see FIG. 2A), there can be more bone contact between the fins and increased fixation, among other possible advantages. The fins 63 and 65 as shown have an angled posterior end for ease of insertion and a plurality of angled slots for improved bone fixation.

The superior and inferior endplates 33 and 35 can be configured to be arranged within a disc space to provide motion in the flexion/extension direction up to a predetermined angle. In one example, the predetermined angle is about ±5 to ±15 degrees, and preferably about ±12 degrees of motion in the flexion/extension direction, i.e., relative angular movement of the anterior and posterior ends 33a and 33p of the superior endplate with respect to the anterior and posterior ends 35a and 35p of the inferior endplate. In a presently preferred disc system, for implants placed with the center of the concave bearing surfaces 47, 49 of the endplates of the two discs 27 and 29 of the disc system about 22 mm apart, the following kinematics can be expected: ±5 degrees of axial rotation and ±12 degrees of flexion/extension. The intervertebral disc system self centers due to the fact that as the core moves away from a neutral centered position, the assembled height of the system gradually increases. The force of the surrounding tissue tries to bring the disc back to the lower height configuration of the neutral position.

Figure 4A:
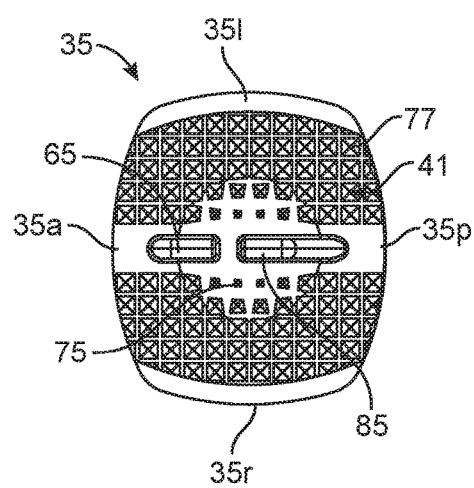
FIGS. 4A-4E are top, bottom, side, anterior cross-sectional, and side cross-sectional views, respectively, of an inferior endplate of an intervertebral disc according to an aspect of the present invention.
Figure 4B:
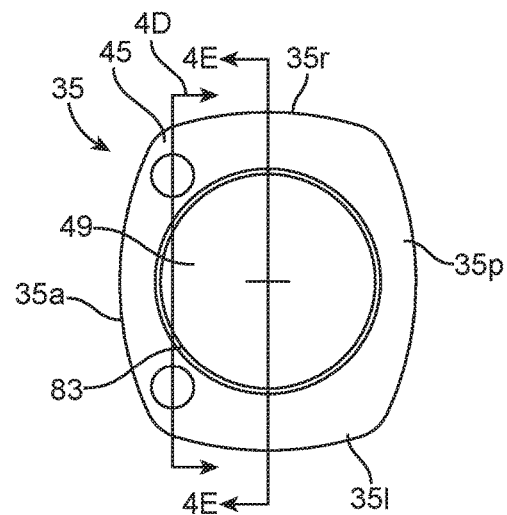

As seen in FIGS. 3B and 4B, the endplates 33 and 35 can be provided with holes or recesses 91 at an anterior end of the endplates to facilitate removal of the endplates anteriorly in a subsequent surgical procedure if needed.

Figure 4C:
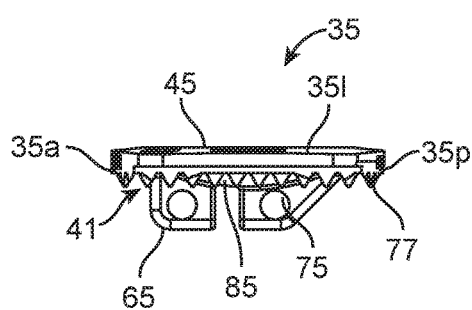
Figure 4D:
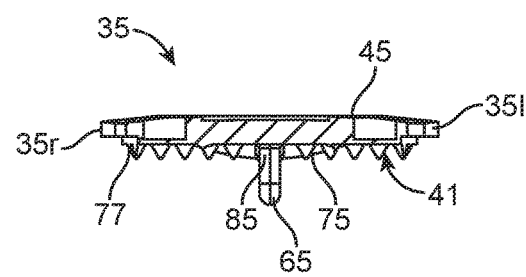
Figure 4E:
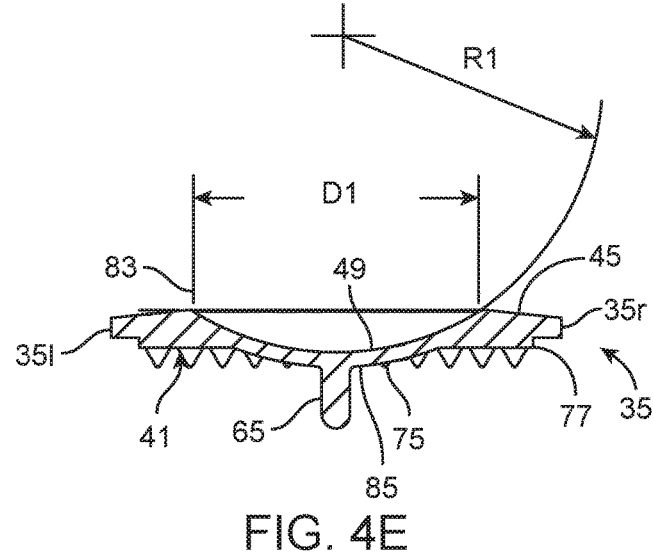
Figure 5:
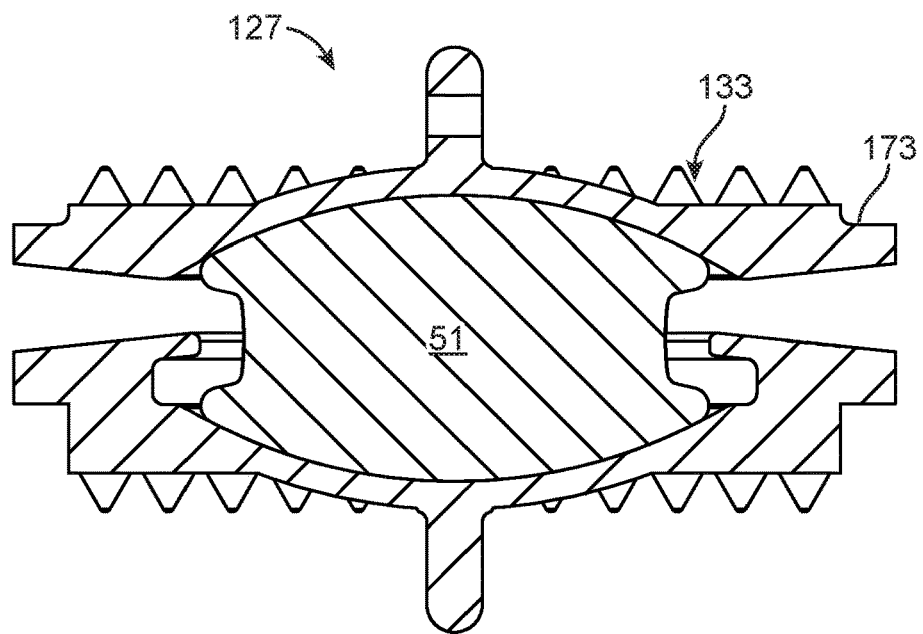
FIG. 5 is a side cross-sectional view of an intervertebral disc according to the prior art.
Figure 6A:
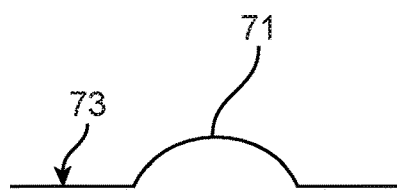
FIGS. 6A, 6B, and 6C illustrate several of various possible geometries for raised central portions of a superior endplate according to aspects of the present invention.
Figure 6B:
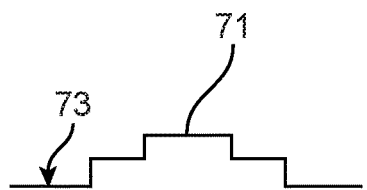
Figure 6C:
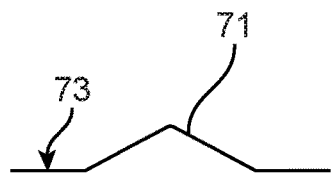

The upper vertebral contacting surface 39 of the superior endplate 33 (FIGS. 3A-3E) has a central portion 71 that is raised relative to a peripheral portion 73 of the superior endplate. As seen in, e.g., FIGS. 2B and 3C-3E, the central portion 71 can be raised so that it defines a portion of a sphere, however, as seen in FIGS. 4A-4C, the raised central portion can have generally spherical (FIG. 6A), stepped (FIG. 6B), or pyramidal or conical (FIG. 6C) shape, as well as other shapes that might be determined to be useful. These shapes are described without considering the shape of the keel 63 which will ordinarily also extend upwardly from the raised central portion 71. The lower bearing surface 47 of the superior endplate 33 ordinarily has a concavity disposed opposite the raised central portion 71.

The lower vertebral contacting surface 41 of the inferior endplate 35 (FIGS. 4A-4E) has a central portion 75 and the upper bearing surface 49 of the inferior endplate also ordinarily has a concavity disposed opposite the central portion. The central portion 75 of the inferior endplate 35 is ordinarily either not raised or not raised to as great an extent relative to the peripheral portion 77 of the inferior endplate as the central portion 71 of the superior endplate 33 is raised relative to the peripheral portion 73 of the superior endplate. Thus, the shape of the upper vertebral contacting surface 39 of the superior endplate 33 is ordinarily different than the shape of the lower vertebral contacting surface 41 of the inferior endplate 35. When the central portion 75 of the inferior endplate 35 is raised, like the raised central portion 71 of the superior endplate 33, it can have generally spherical (FIG. 6A), stepped (FIG. 6B), or pyramidal or conical (FIG. 6C) shape, as well as other shapes that might be determined to be useful.

The height of the superior endplate 33 measured from an outer peripheral edge 79 of the lower bearing surface 47 of the superior endplate to a top 81 of the raised central portion 71 of the upper vertebral contacting surface 39 is ordinarily greater than a height of the inferior endplate 35 measured from an outer peripheral edge 83 of the upper bearing surface 49 of the inferior endplate to a bottom 85 of the central portion 75 of the lower vertebral contacting surface 41. The superior endplate 33 height is ordinarily at least 30% greater than the inferior endplate 35 height. The central portion 75 of the inferior endplate 35 is ordinarily at least somewhat raised, and the raised central portion 71 of the superior endplate 33 ordinarily has a height which is about 150% to 300% of a height of the central portion of the inferior endplate.

The lower bearing surface 47 and the upper bearing surface 49 ordinarily each comprise generally circular outer peripheral edges 79 and 83. The outer peripheral edge 83 of the upper bearing surface 49 can have a larger diameter D1 (FIG. 4E) than the diameter D2 (FIG. 3E) of the outer peripheral edge 79 of the lower bearing surface 47.

The upper vertebral contacting surface 39 of the superior endplate 33 and the lower vertebral contacting surface 41 of the inferior endplate 35 may, in addition to the keels 63 and 65, be provided with knurling, teeth, serrations or some other textured surface 67 to increase friction between the vertebral contacting surfaces and the adjacent vertebra. As seen, for example, in FIGS. 2A and 3A, the textured surface 67 can include a plurality of ribs 69 on the upper vertebral contacting surface 39 of the superior endplate 33 that can extend onto the raised central portion 71 of the superior endplate. The raised central portion 71 of the superior endplate 33 is raised relative to what is ordinarily a generally flat, planar peripheral portion 73 of the superior endplate, although the peripheral portion may have a slight slope away from the raised central portion. The teeth and ribs 69 or other structures of the textured surface extend upwardly from the generally planar peripheral portion 73 of the superior endplate 33. The lower vertebral contacting surface 41 of the inferior endplate 35 may also have a textured surface, such as at least one of teeth and ribs extending downwardly from the generally planar peripheral portion 77 of the inferior endplate.

The upper bearing surface 49 and the lower bearing surface 47 ordinarily each comprise part surfaces of spheres (ordinarily but not necessarily having the same radius R1) with generally circular outer peripheral edges 83 and 79. A core retention portion comprises a wall 61 extending one of downwardly from the outer peripheral edge 79 of the lower bearing surface 47 (shown in FIG. 3E) and upwardly from the outer peripheral edge 83 of the upper bearing surface 49.

The upper and lower core bearing surfaces 53 and 55 of the core 51 ordinarily each comprise generally circular outer peripheral edges 87 and 89, respectively, and the core can have a non-spherical transition region 91 between the upper and lower core bearing surfaces. The recess 59 can be provided in the transition region 91, such as in the form of an annular groove, and the projection 57 can extend inwardly from the wall 61, such as in the form of an annular protrusion. A height of the transition region 91 between the upper and lower core bearing surfaces 53 and 55 is greater than a height of the wall 61 of the core retention portion.

By providing the raised central portion 71 on the upper vertebral contacting surface 39 of the superior endplate 33, the disc 27 can have a reduced height B relative to a disc height C of a conventional disc 127 in which both upper and lower vertebral body contacting surfaces of are flat, as seen by comparing FIGS. 1A and 1B and 2C and 5. The inventor has recognized that the prior art flat configuration does not generally match the surfaces of the vertebral bodies, which results in less than ideal bone to implant contact surfaces. The superior endplate 33 with the raised central portion 71 provides a more anatomically shaped vertebral body contacting surface for an artificial disc while providing the same endplate to endplate spacing A and an equal range of motion. As seen in FIG. 1A, by lowering the periphery 73 of the upper vertebral contacting surface 39 of the superior endplate 33 relative to the periphery 173 of a conventional superior endplate 133, the upper vertebra 200 is allowed to settle into a lower position relative to the lower vertebra. This can, moreover, be accomplished without changing the clearance (ROM) between endplates or the position of the centers of rotation of the endplates. The raised central portion 71 can, in addition, facilitate fixation because the raised central portion can sit deeper into vertebra behind the external cortex, so it is less likely to expulse or retropulse.

The inventor has also recognized that, when the central portions 71 and 75 of both the upper vertebral contacting surface 39 and the lower vertebral contacting surface 41 are raised, it can be advantageous to have the central portions be raised in different amounts, i.e., domes on both endplates are not equal because the anatomy of the upper and lower surfaces of the vertebrae are of different shapes.

Figure 7:
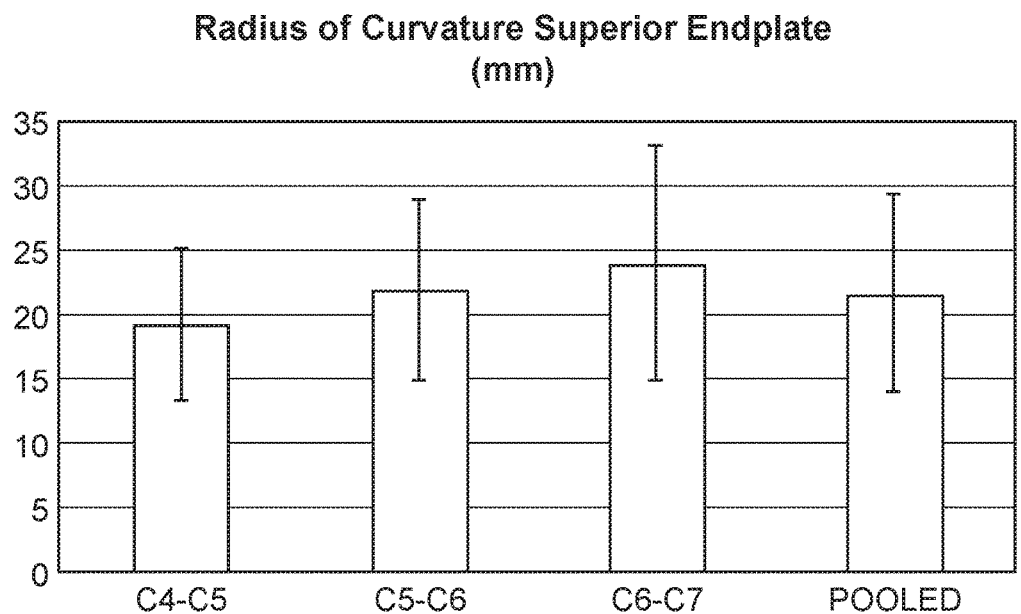
FIG. 7 is a graph of the average radius of curvature of the superior endplate for a collection of patients separated by disc level.
Figure 8:
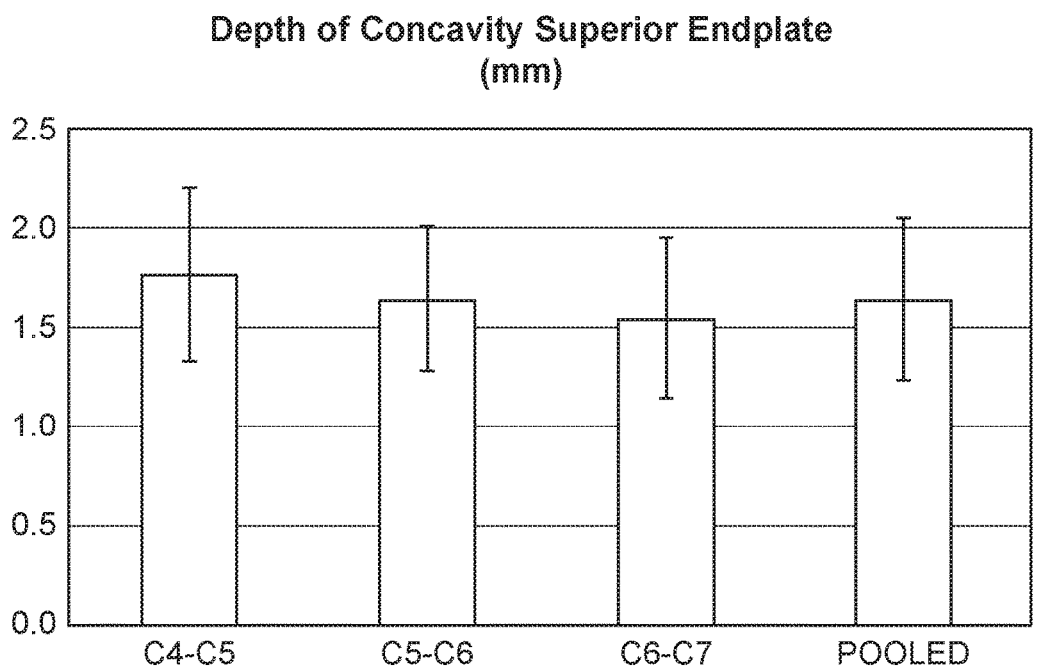
FIG. 8 is a graph of the average depth of the superior endplate concavity for a collection of patients separated by disc level.

FIG. 7 shows the radius of curvature of the superior endplate of the sampling of patients to be between about 10 mm and 30 mm with an average value of about 20 mm FIG. 7 shows the curvatures of different disc levels with the vertebrae identified by numbers C4-C7 and the vertebral spaces identified by the numbers of the two adjacent vertebrae. FIG. 8 shows corresponding numbers for depths of the superior endplate cavities. As a comparison, the inferior endplates were found to be substantially flat or having such a small curvature that it was generally immeasurable. Based on this data and the interest in designing a smaller height disc, the central portion of the superior endplate 71 has been raised by a greater amount than that of the inferior endplate to most closely accommodate the patient anatomy.

The superior and inferior endplates of the two discs may be constructed from any suitable metal, alloy or combination of metals or alloys, such as but not limited to cobalt chrome alloys, titanium (such as grade 5 titanium), titanium based alloys, tantalum, nickel titanium alloys, stainless steel, and/or the like. They may also be formed of ceramics, biologically compatible polymers including PEEK, UHMWPE, PLA or fiber reinforced polymers. The endplates may be formed of a one piece construction or may be formed of more than one piece, such as different materials coupled together.

The core can be made of low friction materials, such as titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. High friction coating materials can also be used.

Different materials may be used for different parts of the disc to optimize imaging characteristics. PEEK endplates may also be coated with titanium plasma spray or provided with titanium screens for improved bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof. Any suitable technique may be used to couple materials together, such as snap fitting, slip fitting, lamination, interference fitting, use of adhesives, welding and/or the like.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. An intervertebral disc comprising:
   a first endplate having a vertebra contacting surface and an opposite bearing surface, wherein the vertebra contacting surface of the first endplate has a domed central portion and wherein the bearing surface has a concavity disposed opposite the domed central portion, and wherein the domed central portion is raised relative to a generally planar peripheral portion of the first endplate;
   a second endplate having a vertebra contacting surface and an opposite bearing surface, wherein the vertebra contacting surface of the second endplate has a domed central portion with a diameter different than the domed central portion of the first endplate;
   a core positioned between the first and second endplates, the core having first and second surfaces configured to mate with the bearing surface of the first endplate and the bearing surface of the second endplate, respectively; and
   a plurality of ribs provided on the vertebra contacting surface of the first endplate, wherein the ribs extend onto the domed central portion of the first endplate.

2. The disc of claim 1, wherein the first endplate comprises a keel extending outward from the domed central portion.

3. The disc of claim 1, comprising a textured surface provided on the vertebra contacting surface of the first endplate and the vertebra contacting surface of the second endplate.

4. The disc of claim 1, wherein the bearing surface of the second endplate has a concavity disposed opposite the domed central portion, and wherein a plurality of ribs are provided on the vertebra contacting surface of the second endplate and the ribs extend onto the domed central portion of the second endplate.

5. The disc of claim 4, wherein the domed central portion of the first endplate has a different shape than the central dome of the second endplate.

6. The disc of claim 1, further comprising a plurality of teeth extending outward from the first and second endplates.

7. The disc of claim 1, wherein the first and second surfaces of the core comprise part surfaces of spheres.

8. The disc of claim 1, wherein the plurality of ribs are elongated in a direction extending between transverse side surfaces of the disc.

9. The disc of claim 1, further comprising a central keel provided on the vertebra contacting surface of at least one of the first and second endplates, the central keel extending in an anterior/posterior direction.

10. An intervertebral disc comprising:
    a first endplate having a vertebra contacting surface and an opposite bearing surface, wherein the vertebra contacting surface of the first endplate has a domed central portion which is raised relative to a generally planar peripheral portion of the first endplate and wherein the bearing surface of the first endplate has a concavity disposed opposite the domed central portion;
    a second endplate having a vertebra contacting surface and an opposite bearing surface, wherein the vertebra contacting surface of the second endplate has a domed central portion which is raised relative to a generally planar peripheral portion of the second endplate and wherein the bearing surface of the second endplate has a concavity disposed opposite the domed central portion; and
    a core positioned between the first and second endplates, the core having first and second surfaces configured to mate with the bearing surfaces of the first and second endplates, respectively;
    wherein an outer periphery of the vertebra contacting surface central dome of the first endplate has a larger diameter than an outer periphery of the vertebra contacting surface central dome on the second endplate to accommodate patient anatomy.

11. The disc of claim 10, comprising at least one of teeth and ribs extending outward from the generally planar peripheral portions of the first and second endplates.

12. The disc of claim 10, wherein the bearing surfaces of the first and second endplates each comprise generally circular outer peripheral edges.

13. The disc of claim 12, wherein the outer peripheral edge of the bearing surface of the first endplate has a larger diameter than the outer peripheral edge of the bearing surface of the second endplate.

14. An intervertebral disc comprising:
    a first endplate having a vertebra contacting surface and an opposite bearing surface, wherein the vertebra contacting surface of the first endplate has a domed central portion, wherein the bearing surface has a concavity disposed opposite the domed central portion, and wherein the domed central portion of the first endplate is raised relative to a generally planar peripheral portion of the first endplate surrounding the domed central portion;
    a second endplate having a vertebra contacting surface and an opposite bearing surface, wherein the vertebra contacting surface of the second endplate has a domed central portion with a diameter different than the domed central portion of the first endplate;
    a core positioned between the first and second endplates, the core having first and second surfaces configured to mate with the bearing surface of the first endplate and the bearing surface of the second endplate, respectively; and
    a keel extending outwardly from the domed central portion of the first endplate, wherein the keel is elongated in an anterior/posterior direction of the disc.

15. The disc of claim 14, comprising a textured surface provided on the vertebra contacting surface of the first endplate and the vertebra contacting surface of the second endplate.

16. The disc of claim 14, wherein the vertebra contacting surface of the second endplate has a domed central portion and the bearing surface has a concavity disposed opposite the domed central portion.

17. The disc of claim 16, wherein the domed central portion of the first endplate has a different shape than the central dome of the second endplate.

18. The disc of claim 16, wherein a keel extends outwardly from the domed central portion of the second endplate and the second endplate keel is elongated in an anterior/posterior direction of the disc.

* * * * *